(12) United States Patent
Goldfeld et al.

(10) Patent No.: US 9,051,535 B2
(45) Date of Patent: Jun. 9, 2015

(54) PROTEIN-ENHANCED SURFACTANTS FOR ENZYME ACTIVATION

(71) Applicant: ADVANCED BIOCATALYTICS CORP., Irvine, CA (US)

(72) Inventors: Michael G. Goldfeld, Irvine, CA (US); Andrew H. Michalow, Irvine, CA (US); Carl W. Podella, Irvine, CA (US); John W. Baldridge, Irvine, CA (US)

(73) Assignee: ADVANCED BIOCATALYTICS CORPORATION, Irvine, CA (US)

( * ) Notice: Subject to any disclaimer, the term of this patent is extended or adjusted under 35 U.S.C. 154(b) by 0 days.

(21) Appl. No.: 13/851,033

(22) Filed: Mar. 26, 2013

(65) Prior Publication Data

US 2013/0252287 A1    Sep. 26, 2013

Related U.S. Application Data

(60) Provisional application No. 61/615,805, filed on Mar. 26, 2012.

(51) Int. Cl.

| | |
|---|---|
| C12N 9/96 | (2006.01) |
| C11D 3/386 | (2006.01) |
| C12P 19/02 | (2006.01) |
| C11D 3/38 | (2006.01) |
| C12P 19/14 | (2006.01) |
| C12P 21/00 | (2006.01) |
| C12N 9/20 | (2006.01) |
| C12P 7/64 | (2006.01) |
| C12N 9/42 | (2006.01) |

(52) U.S. Cl.
CPC ........ C11D 3/38627 (2013.01); C11D 3/38645 (2013.01); C12P 19/02 (2013.01); C11D 3/38 (2013.01); C11D 3/38636 (2013.01); C12P 19/14 (2013.01); C12P 21/00 (2013.01); C12N 9/20 (2013.01); C12N 9/96 (2013.01); C12P 7/6418 (2013.01); C12N 9/2437 (2013.01)

(58) Field of Classification Search
None
See application file for complete search history.

(56) References Cited

U.S. PATENT DOCUMENTS

| | | |
|---|---|---|
| 2,320,478 A | 6/1943 | Sperti |
| 2,320,479 A | 6/1943 | Sperti |
| 4,169,817 A | 10/1979 | Weber |
| 5,292,448 A | 3/1994 | Klugkist |
| 5,447,649 A | 9/1995 | Gormsen |
| 5,614,484 A | 3/1997 | Panandiker |
| 5,707,950 A | 1/1998 | Kasturi et al. |
| 5,776,441 A | 7/1998 | Scancarella et al. |
| 5,833,066 A | 11/1998 | Hargus et al. |
| 5,851,973 A | 12/1998 | Foley |
| 5,883,066 A | 3/1999 | Herbots et al. |
| 5,935,271 A | 8/1999 | Lappas et al. |
| 5,955,416 A * | 9/1999 | Baillely et al. ............... 510/357 |
| 5,967,157 A | 10/1999 | Chatterjee et al. |
| 6,017,866 A | 1/2000 | Aehle et al. |
| 6,066,611 A | 5/2000 | Ghosh et al. |
| 6,071,356 A | 6/2000 | Olsen |
| 6,133,227 A | 10/2000 | Barnabas et al. |
| 6,140,295 A | 10/2000 | Behan et al. |
| 6,322,595 B1 | 11/2001 | Boyer |
| 6,436,696 B1 | 8/2002 | Hsieh et al. |
| 6,465,410 B1 | 10/2002 | Bettiol et al. |
| 6,468,955 B1 | 10/2002 | Smets et al. |
| 6,624,132 B1 | 9/2003 | Man et al. |
| 6,858,212 B2 | 2/2005 | Scholz et al. |
| 6,881,712 B2 | 4/2005 | Angell et al. |
| 7,156,514 B2 | 1/2007 | Rosa |
| 7,165,561 B2 | 1/2007 | Baldridge et al. |
| 7,297,224 B2 | 11/2007 | Nakamura et al. |
| 7,374,921 B2 | 5/2008 | Okakura et al. |
| 7,419,809 B2 | 9/2008 | Foody et al. |
| 7,476,529 B2 | 1/2009 | Podella et al. |
| 7,569,528 B2 | 8/2009 | Lant et al. |
| 7,604,967 B2 | 10/2009 | Yang et al. |
| 7,645,730 B2 | 1/2010 | Baldridge et al. |
| 7,659,237 B2 | 2/2010 | Baldridge et al. |
| 7,709,436 B2 | 5/2010 | Theiler et al. |

(Continued)

OTHER PUBLICATIONS

Podella & Baldridge, "Changing the Nature of Surfactants", Industrial Biotechnology, 2005, 1:288-291.*

(Continued)

*Primary Examiner* — Suzanne M Noakes

(74) *Attorney, Agent, or Firm* — Sam K. Tahmassebi; TechLaw LLP

(57) ABSTRACT

Disclosed herein are compositions containing enzymes, particularly acting at the interface between two immiscible phases where the rate of enzymatic activity is increased by addition of a blend of surfactant(s) and a mixture derived from yeast fermentation, that contain non-enzymatic exo-proteins released by yeast in response to a non-lethal stress. The enzymes include those that work at the interface between an aqueous solution and a water immiscible phase, liquid or solid, such as oil, fat, cellulose, lignin, etc. including, but not limited to the following or combinations thereof: lipases, polysaccharase, lignase, cellulase and the like, in which the substrate of an enzymatic reaction forms a phase, segregated from the aqueous solution in which the enzymes are typically operating. Disclosed herein are methods for improving a washing solution with the use of these compositions, where the enzyme-protein-surfactant solution can be used in such applications as: laundry, spot remover, pre-laundry, dishes, hard surface cleaning, wastewater treatment, cellulose breakdown as in ethanol production, lignin utilization, environmental remediation, industrial cleaning, and agricultural applications.

19 Claims, 3 Drawing Sheets

(56) References Cited

U.S. PATENT DOCUMENTS

| | | | |
|---|---|---|---|
| 7,741,093 | B2 | 6/2010 | Vehmaanpera et al. |
| 7,759,301 | B2 | 7/2010 | Baldridge et al. |
| 7,790,666 | B2 | 9/2010 | Souter et al. |
| 7,902,138 | B2 | 3/2011 | Ouwendijk-Vrijenhoek et al. |
| 8,110,389 | B2 | 2/2012 | Lavigne et al. |
| 2002/0032142 | A1 | 3/2002 | Smets et al. |
| 2009/0217463 | A1 | 9/2009 | Souter et al. |
| 2010/0162491 | A1 | 7/2010 | Souter et al. |
| 2011/0237486 | A1 | 9/2011 | Souter et al. |

OTHER PUBLICATIONS

Podella et al., "Yeast protein-surfactant complexes uncouple microbial electron transfer and increase transmembrane leak of protons", Journal of Applied Microbiology, 2009, 106: 140-148.*

Diaz et al., Effect of nonionic surfactants on *Rhizopus homothallicus* lipase activity. A comparative kinetic study. Mol Biotechnol. Mar. 2007;35(3):205-214.

Duzhak et al., [Isolation and properties of extracellular lipase of native (B-10) and mutant (M-1) *Serratia marcescens* strains]. Prikl Biokhim Mikrobiol. Jul.-Aug. 2000;36(4):402-411 (Engl abstract only).

Eriksson et al., Mechanism of surfactant effect in enzymatic hydrolysis of lignocelluloses. Enzyme and Microbial Technology 31(3). p. 353-364.

Ghose, Measurement of Cellulase Activities. Pure Appl Chem. 1987;59(2):257-268.

Helle et al., Effect of surfactants on cellulose hydrolysis. Biotechnol Bioeng. Aug. 20, 1993;42(5):611-617 (abstract only). Also accessed at: http://onlinelibrary.wiley.com/doi/10.1002/bit.260420509/abstract.

Hermoso, et al., Lipase Activation by Nonionic Detergents. The Crystal Structure of the Porcine Lipase-Colipase-Tetraethylene Glycol Monooctyl Ether Complex. J Biol Chem. Jul. 26, 1996;271(30):18007-18016.

Jurado, et al., Hard-Surface Cleaning Using Lipases: Enzyme—Surfactant Interactions and Washing Tests. J Surfact Deterg Jan. 16, 2007;10:61-70. Accessed online at: http://lib3.dss.go.th/fulltext/Journal/J.Surfactants%20and%20Detergents/no.1/2007v10n1p61-70.pdf.

Kregel , Heat shock proteins: modifying factors in physiological stress responses and acquired thermotolerance. J Appl Physiol (1985). May 2002;92(5):2177-2186.

Liu et al., Enhancing effect of Tween-80 on lipase performance in enantioselective hydrolysis of ketoprofen ester. J Molec Catalysis B: Enzymatic. 2000;10(5):523-529.

Nielsen et al., Household & Personal Products Industry—How enzymes can reduce the impact of liquid detergents: one cost-neutral solution is to replace surfactants with a multienzyme solution that improves the environmental impact of a liquid laundry detergent without compromising performance . Happi Household and Personal Products Industry Sep. 7, 2010:1-7 accessed online at http://www.happi.com/issues/2010•09/view_features/how•enzymes•can•reduce•the•environmenta•impa/.

Pernas et al., Regulation of the interfacial activation within the *Candida rugosa* lipase family. J Phys Organic Chem. 2009;22(5):508-514.

Polizelli et al., Effect of Surfactants and Polyethylene Glycol on the Activity and Stability of a Lipase from Oilseeds of *Pachira aquatica*. J Amer Oil Chem Soc.2008;85:749-753.

Skagerlind et al., Lipase-surfactant interactions. The Colloid Science of Lipids. Progress in Colloid & Polymer Sci. 1998;108:47-57.

Thakar and Madamwar, Enhanced ethyl butyrate production by surfactant coated lipase immobilized on silica. Process Biochem. 2005;40(10):3263-3266.

Yamada et al., Increased Activity of *Chromobacterium viscosum* Lipase in Aerosol OT Reverse Micelles in the Presence of Nonionic Surfactants. Biotechnol Prog. Sep.-Oct. 1993;9(5):468-472.

* cited by examiner

PROTEIN-ENHANCED SURFACTANTS FOR ENZYME ACTIVATION

RELATED APPLICATIONS

This application claims priority to U.S. Provisional Application No. 61/615,805, filed Mar. 26, 2012, by Michael G. Goldfeld, et al., and entitled "PROTEIN-ENHANCED SURFACTANTS FOR ENZYME ACTIVATION," which is incorporated herein by reference in its entirety.

FIELD OF THE INVENTION

The present invention is in the field of enzymes, non-enzymatic yeast proteins and surfactants, and applications of their combinations.

BACKGROUND OF THE DISCLOSURE

Enzymes when exposed to certain chemicals, are prone to denaturing or inactivation. In particular, U.S. Pat. No. 6,017,866 states that: "Important stability problem is the sensitivity of enzymes towards denaturation by anionic, cationic or nonionic surfactant molecules".

On the other hand, some enzymes, as e.g. lipases, are activated by certain surfactants [Lipase Activation by Nonionic Detergents. Juan Hermoso, et al., (1996) J. Biol. Chem, v. 271, pp. 18007-18016], while anionic surfactants, proved to be inhibitory [Enhanced ethyl butyrate production by surfactant coated lipase immobilized on silica. Amit Thakar, et al. (2005) Process Biochemistry, v. 40(10) pp. 3263-3266; Effect of nonionic surfactants on *Rhizopus homothallicus* lipase activity. A comparative kinetic study. J. C. Mateos Diaz, et al. Molecular Biotechnology, v. 35(3), pp. 205-214; Isolation and properties of extracellular lipase of native (B-10) and mutant (M-1) *Serratia marcescens* strains]. Duzhak A B, et al. (2000) Prikl Biokhim Mikrobiol. v. 36(4), pp. 402-11; Increased activity of *Chromobacterium viscosum* lipase in aerosol OT reverse micelles in the presence of nonionic surfactants. Yasushi Yamada, et al. (1993) Biotechnol. Prog., v. 9(5), pp 468-472; Effect of Surfactants and Polyethylene Glycol on the Activity and Stability of a Lipase from Oilseeds of *Pachira aquatica*. Patricia Peres Polizelli, et al., J. Amer. Oil Chem. Soc. v. 85(8), pp. 749-753]. Lipases are used in a number of industries and applications: laundry, dishes, hard surface cleaning, wastewater treatment, water or soil remediation, industrial applications, enhanced oil recovery, textile processing, agricultural chemicals, flavor industry, biocatalytic resolution of pharmaceuticals, production and processing of esters and amino acid derivatives, cosmetics, and skin and hair care applications.

Enzymes have been used for cleaning in industrial applications. U.S. Pat. No. 4,169,817 teaches that, " . . . the enzyme-containing liquid detergent composition has a particular and important use in cleaning semi-permeable membranes used in reverse osmosis processes. The membranes are generally composed of cellulose acetate, and the detergent composition can be utilized in a clean-in-place operation to remove clogged material from the pores of the membrane." U.S. Pat. No. 7,165,561 discloses methods to clean fouled cross-flow membrane systems, including reverse osmosis.

When enzymes are used in detergent formulations, surfactants have to be chosen carefully as it has been found that, e.g., nonionic surfactants can reduce the effectiveness of certain enzymes: "Nonionic surfactants seem to prevent or delay enzyme penetration at the interface, thereby decreasing lipase activity." (Jurado, 4) It has been shown, as in U.S. Pat. No. 7,645,730, that compounds from the yeast extracts bind with surfactants and these combinations displayed increased surface activity towards oil, other hydrophobic organic substrates and some odorous substances.

U.S. Pat. No. 6,071,356 discloses the combination of lipase and protease for cleaning in place for industrial equipment, including membranes, mostly in food processing industries, and by using enzymes the amount of water and surfactants can be reduced.

Cellulase hydrolyzes celluloses and cellulolytic enzymes are used in a number of industrial and consumer products. For example, the addition of cellulase into detergent formulations has been shown to improve their efficacy. However, U.S. Pat. No. 5,833,066 teaches that: " . . . in anionic surfactant liquid detergent compositions the stability of enzymes, in particular cellulases is greatly reduced."

Cellulases are also used in fabric treatment to create the "stone washed" look of denim, de-inking of fabrics, and removing fuzz from cotton fabrics. They are also used to prevent clogging of ink in print heads, U.S. Pat. No. 7,156,514 (Rosa), de-inking of waste paper, in glucose production by enzymatic action on cellulosics and other uses.

SUMMARY OF THE INVENTION

Disclosed herein are compositions comprising non-enzymatic exo-proteins, a surfactant and an enzyme. Also disclosed are methods of accelerating the rate of lipase activity in the removal and degradation of oily contamination from a surface or solution comprising contacting the surface with the above compositions. Also disclosed are methods of increasing catalytic activity of an interfacial hydrolytic and/or oxidizing enzyme with substrates forming a water-immiscible segregated phase, the method comprising contacting the enzyme with the above compositions.

DETAILED DESCRIPTION OF THE EMBODIMENTS

Figure 1:
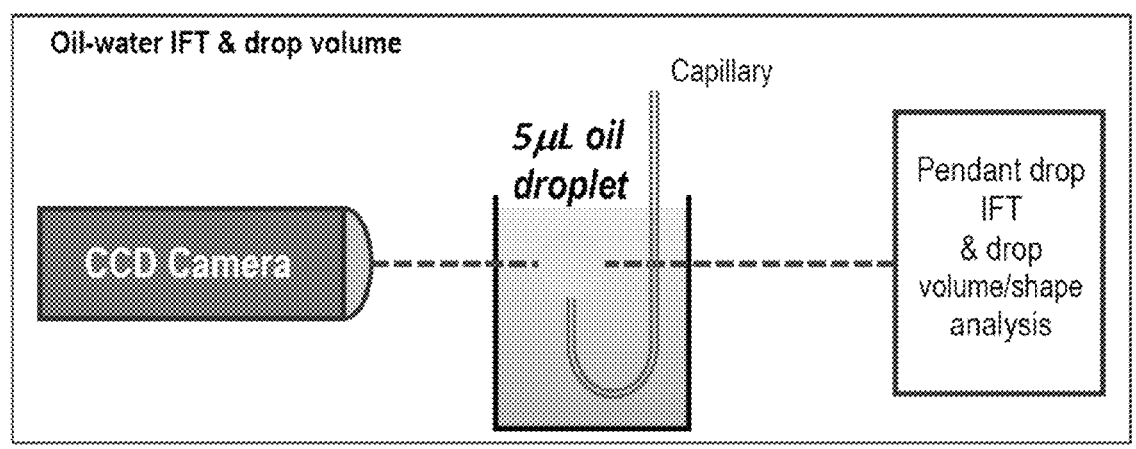
FIG. 1 is a diagram of the experimental set up.

Yeast extracts disclosed herein, containing living yeast exo-proteins, were developed to take advantage of a synergy that was found between certain non-enzymatic yeast exo-proteins and surfactants, where the functionality of such a blend can be further enhanced in some instances with the addition of certain enzymes. Enzymes are being used increasingly in consumer products, such as cleaners, cloth and dish washing detergents, etc., as well as in many industrial applications such as industrial cleaning, wastewater treatment, cellulose breakdown for ethanol and biofuel production, odor elimination, textile processing, agriculture and more.

Factors that are driving the growth of enzyme applications include their specificity, high degree of biodegradability, low environmental impact, and ability to offset other costs, such as reducing certain process temperatures, reducing surfactant levels, etc. However, the cost of enzymes is relatively high and limits their use. The presently disclosed methods and compositions are directed to how a mixture of yeast extract and a surfactant can enhance the enzyme activity of enzymes of certain classes.

Any improvement in the performance of enzymes, for example to reduce their concentrations or enhance activity, would help to broaden their uses.

In the context of the present disclosure, "cleaning" can be summarized as the removal and/or neutralization of undesirable soils from surfaces, and is defined by its most fundamental features: the removal, or lifting from a surface, or neutralization, of organic, inorganic and biologically based compounds or entities, that create or lead to: (a) unsanitary conditions, (b) unpleasant aesthetics such as stains and dirt, (c) odors, (d) biofilms, (e) impede or disrupt mechanical, chemical and biochemical processes, or (f) crude oil entrapment in underground mineral deposits.

The term "surfaces" can refer to either hard surfaces, such as floors, equipment, shelves, automobiles, minerals in the ground (oil recovery), and the like, or soft surfaces, such as fabrics and textiles, or even cleaning up water itself.

Objectionable soils include entities such as, oils and greases, mineral deposits, bacterial and viral substances and their secretions, organic compounds both naturally and synthetically derived, malodorous compounds, and combinations of the above.

Soiling includes organic substances that act as a breeding ground for microbial growth, be it bacterial, fungal, algae, etc., or their secretions. As examples, cleaning floors and equipment can include biofilm control such as biofilm growth in porous surfaces, in paper processing, in cleaning cross-flow membranes such as reverse osmosis, micro-filtration and ultra-filtration, industrial tank cleaning and sanitizing, cooling system cleaning including cooling towers and condensers.

In laundry and dish detergent formulations, hard surface cleaning, and the like, enzymes are used to replace and reduce the level of surfactants needed (Nielsen, 1). One reason driving this is that many of the typical surfactants used in detergent formulations are difficult to fully break down in wastewater treatment facilities, and subsequently the surfactants wind up in the environment. Surfactants, in general, can be detrimental to aquatic species. For instance, nonyl phenol ethoxylates, widely used in detergents and agricultural adjuvants, are persistent and have been shown to create endocrine mimicking compounds in the environment. Enzymes, however, are readily biodegradable. Further, enzymes provide benefits that include cleaning at lower temperatures, saving on energy costs (1).

The surfactant-enzyme-yeast exo-protein compositions disclosed herein enhance functionality, i.e., increase the efficiency of the cleaning. The enhanced functionality is measured in terms of one or more of: (a) chemical breakdown and solubilization of fats, oils and greases; (b) creation of additional surface active agents during the breakdown of fats and oils yielding cleaning synergy; (c) removal of odors caused by urine, feces, vomit, other biological fluids, rotting food, biofilm slime and other sources; (d) removal and control of biofilms; (e) enhanced biodegradability of waste products associated with the cleaning processes.

In a further embodiment, the compositions of the current invention improve breakdown of cellulosics, starch grains, biological membranes, lignin and the like, for ethanol production, paper and pulp processing.

In one aspect, the methods and compositions disclosed herein relate to enzymes that perform degrading reactions at the interface (hereafter denoted "interfacial enzymes"), such as lipase, cellulose, and, under certain circumstances, also lignase, and other enzymes and enzymatic complexes degrading natural non-water soluble polymeric materials by hydrolytic, oxidative reactions and their combinations.

Yeast Extracts

Yeast exo-proteins are defined as species that are produced by fermentation and any of a number of known processes can be used to produce the exo-proteins, with either aerobic or anaerobic fermentation. Virtually any carbohydrate and nutrient combinations that allow yeast to grow during fermentation can be used. Aerobic processes are preferred due to shorter fermentation times, which can lower costs. Stress proteins are produced by yeast as a response to chemical, thermal, radiation, or mechanical stress that causes certain genes to be expressed by the yeast, therefore stimulating their production of compounds in a fermentation process that can be either anaerobic or aerobic. Yeast extracts have been long known for their use in skin care as live yeast cell derivative, or LYCD as per Sperti in U.S. Pat. Nos. 2,320,478 and 2,320,479, using an alcohol extraction process with baker's yeast that kills the yeast cells used for extraction from alcohol and temperature lysis. The current invention does not require that the yeast be killed, as the exo-proteins are produced by yeast as a response to stress signals. Furthermore, the costs of purifying and isolating LYCD are high and for the purposes of combining the yeast extract with enzymes, the entire supernatant from a yeast fermentation process can potentially be utilized.

In particular, heat has been shown to be a simple, repeatable source of stress for yeast exo-protein production. The processes for the production of stress proteins, and in particular heat shock proteins, is described in U.S. Pat. Nos. 7,476,529, 7,645,730, 7,659,237 and 7,759,301. For example, these patents disclose that: "Prior to centrifugation, the yeast in the fermentation product is subjected to heat-stress conditions by increasing the heat to between 40 and 60 degrees C., for 2 to 24 hours, followed by cooling to less than 25 degrees C." The entire disclosure of the above-referenced patents, in particular the discussion on the production of stress proteins (for example, column 3, line 41 to column 4, line 51 of U.S. Pat. No. 7,659,237) is incorporated by reference herein.

The thermal stress can be done at lower or higher temperatures, depending on the overall process and particular strain of yeast being used. *Saccharomyces* s. can start to die off at about 70.deg.C., and it is assumed that at some point near this temperature they would stop excreting any proteins. Heat shock proteins are also known as stress proteins, a result of exposing yeast to stress conditions that include heat, chemical or mechanical stress. [Heat shock proteins: modifying factors in physiological stress responses and acquired thermotolerance. Kevin C. Kregel (2001) J. Applied Physiol. v. 92(5), pp. 2177-2186] Thus defined, yeast exo-proteins have properties related to the following, with optimal benefits when they contain stress proteins:

(a) improving surfactant performance in terms of lowering interfacial tension, surface tension, critical micelle concentration, improving wetting, penetration and uptake of solutions and their ingredients by various materials, and (b) accelerating microbial, mostly, but not exclusively aerobic, metabolic rates with a mechanism shown to rely, at least partially, on uncoupling of oxidative phosphorylation in bacterial cells.

Experiment 1

Initial tests with lipase were conducted with a protein-surfactant cleaning composition that comprised both anionic and nonionic surfactants. It has been found that the sevenfold increase in lipase activity occurs, as measured by the time it took to digest a droplet of oil/grease down to 5% of its initial volume, (4) Although activation of lipase by synthetic surfactants has been previously known [Regulation of the interfacial activation within the Candida rugosa lipase family. M.A.

Permas, et al. J. Phys. Organic Chem., v.22 (5), pp. 508-514 (2009; Enhancing effect of Tween-80 on lipase performance in enantioselective hydrolysis of ketoprofen ester. You-Yan Liu, et al., J. Molec. Catalysis B: Enzymatic, v.10 (5), pp. 523-529 (2000); see also: [www.xtallqfr.csic.es/grupo/xjuan/lipasa], the enhancement of the activation effect by use of a complex formed between the surfactant(s) and yeast extracts could not be predicted, and, moreover, the involvement of proteins might have both positive, or negative effect on the oil/grease consumption.

Preparation of Enzyme Solutions

Lipase used in these tests was *Candida rugosa* Lipase AY30 powder from ACROS Organics. In all tests below, the amount of lipase was adjusted to the final concentration of 1 mg/mL, buffered at pH 8.2-8.4.

Procedure

The activity of lipase was determined by the extent of consumption of the lipase substrate, such as a standard Peacock Prime Burning Lard Oil, introduced into the system in the form of precisely portioned, droplet with its initial volume of 5 µL. Pendant drop method was applied, with continuous video recording of the volume and shape of the droplet sitting at the tip of a capillary. The information thus produced was further analyzed using specialized software associated with the Kruss Drop Shape Analysis System DSA 10 pendant drop tensiometer, which permits to construct a kinetic graph of the change in both oil droplet volume (as a measure of the progress of the oil consumption) and interfacial tension between oil and water phases. The diagram of the experimental set is shown in FIG. 1.

Each Peacock Oil drop was observed until at least 99% of the drop's volume disappeared.

Sample 1

|  | Example 1 | Example 2 | Example 3 |
|---|---|---|---|
| Yeast Exo-Protein Solution | 20% | 20% | — |
| Alcohol Ethoxylate C9-11 | 12% | — | 12.0% |
| Sodium Dioctylsulfosuccinate | 6% | — | 6.0% |
| Hexylene Glycol | 7% | — | 7.0% |
| EDTA | 1% | — | 1.0% |
| Triethanolamine | 0.5% | 0.5% | 0.5% |
| Water | 53.5% | 80% | 73.5% |

Figure 2:
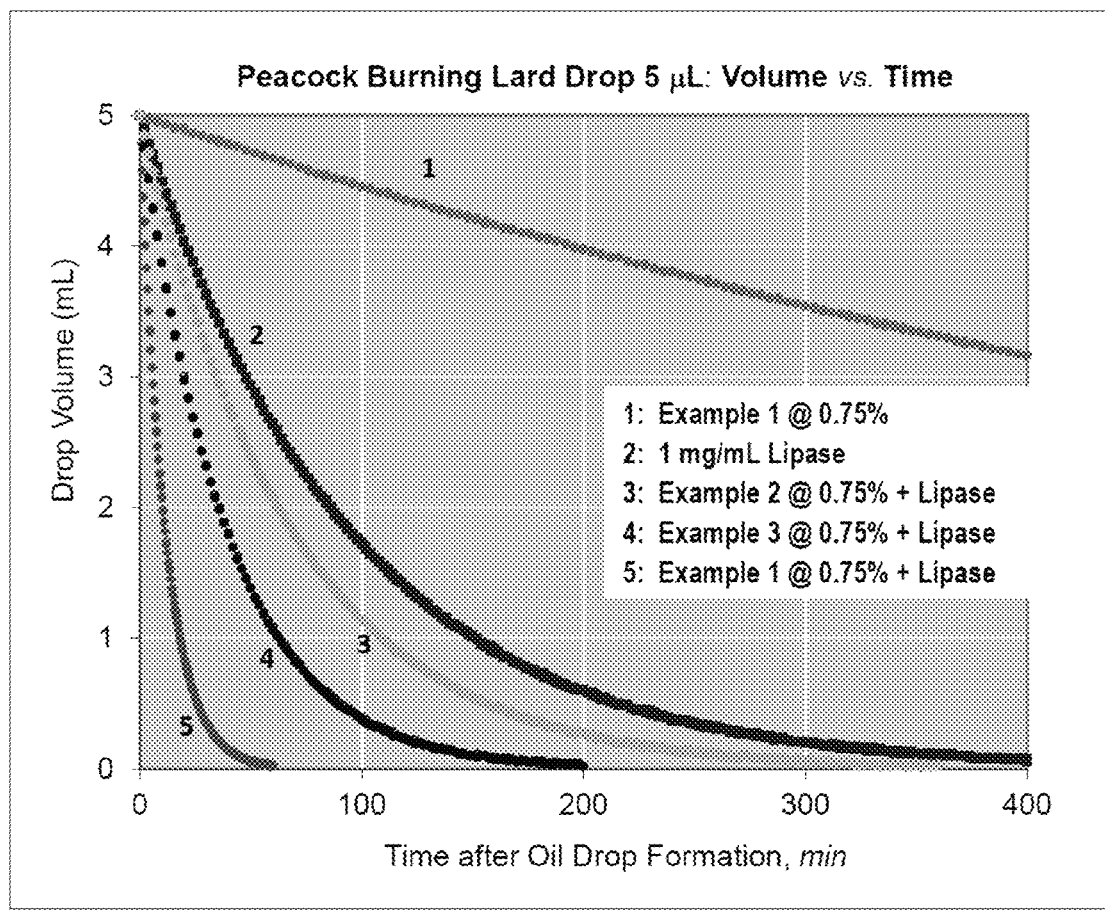
FIG. 2 is a graph that shows the kinetics of oil drop consumption in various systems.

The kinetics of oil drop consumption is shown in FIG. 2. The following systems were studied in terms of their effect on the rate of oil droplet consumption:

Graph #1—Example 1, no lipase

Graph #2—Solution containing 1 mg/mL Lipase;

Graph #3—Solution containing 1 mg/mL Lipase and yeast exo-proteins, Example 2, only from 0.75% Example 1 (but no surfactants).

Graph #4—Solution containing 1 mg/mL lipase in surfactant pack only, i.e. a mixture of the same surfactants, and at the same final concentrations as in 0.75% Example 1 (but do not contain any yeast exo-proteins).

Graph #5—Solution containing 0.75% Example 1, containing both synthetic surfactants (Sf) (anionic and non-ionic) and yeast exo-proteins, as previously defined. This sample does not contain lipase and thus does not have lipolytic activity In FIG. 3, Graphs #5 and #6 (Example 1 only) give a background kinetics for the process of emulsification of the oil droplet in the absence of any lipolytic activity, since it was previously found that yeast exo-proteins do not display lipase activity whatsoever. It is a slow, nearly linear graph, showing only 18% of oil drop reduction in the first 7 hours of experiment (each experiment actually lasted for 16 hours, but we only show the initial phase of it where the differences can be seen the best).

Graph #1 shows the kinetics of the oil consumption in droplet due to regular lipase activity, with 95% of the volume reduction in 7 hours after lipase addition. This is the background enzymatic process unassisted by any surfactant.

Figure 3:
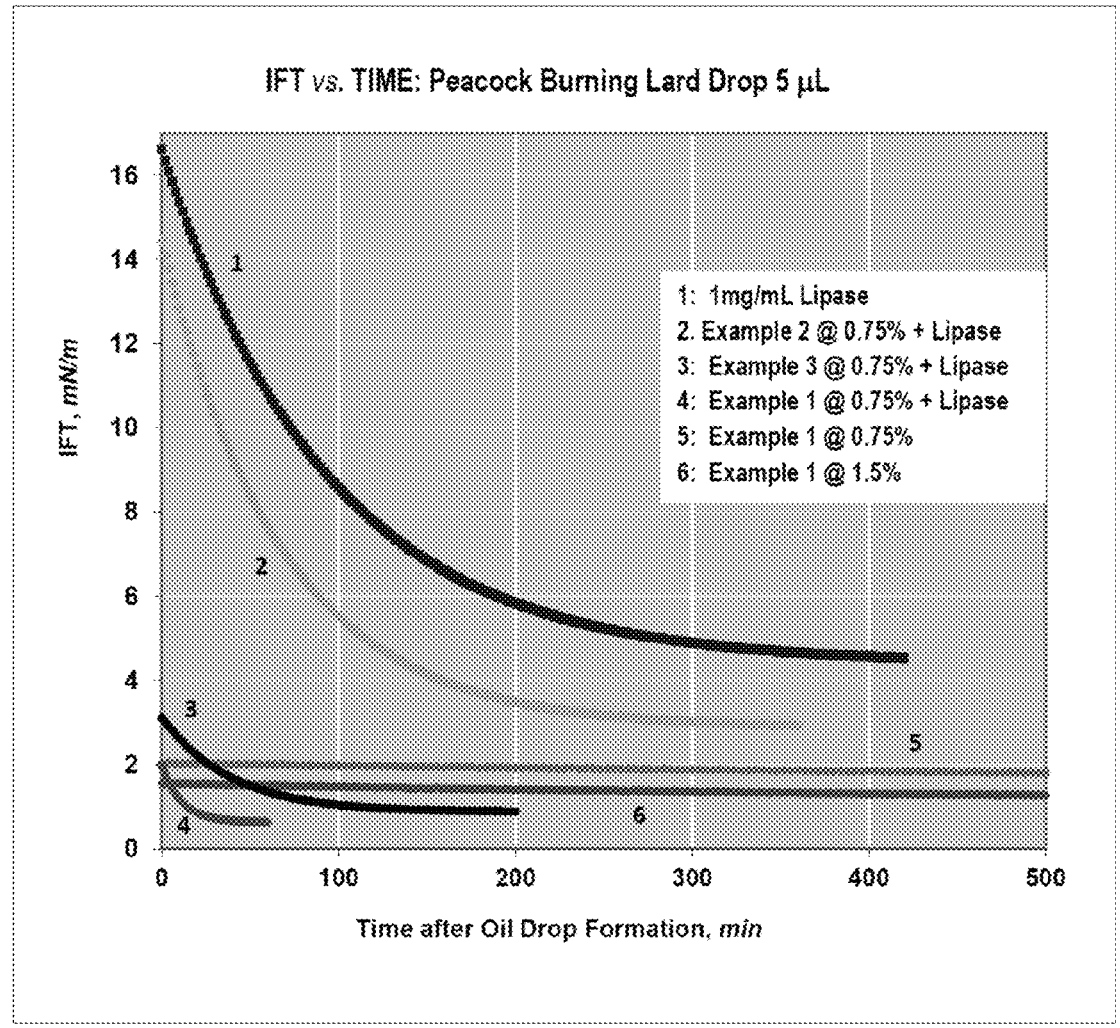
FIG. 3 is a graph that shows the kinetics of IFT reduction in the progress of lipase.

Graph #2 shows the kinetic of oil droplet consumption catalyzed by lipase in the presence of yeast exo-proteins only, but no synthetic surfactant. There still is some acceleration of the drop consumption as compared to the lipase taken alone, although yeast exo-proteins, on their own, do not display significant surface activity: initial interfacial tension decreases from 16.5 mN/m down in lipase solution to 14.5 mN/min the solution containing both lipase and MF (FIG. 3).

Graph #3 shows substantial, about two-fold, acceleration of oil consumption by lipase in the presence of surfactant blend, Example 3, as is expected for this interfacial enzyme: the 95% consumption occurs in about 200 minutes, as compared to 400 minutes in the absence of surfactants.

Graph #4 displays the combined effect of yeast protein and surfactants, Example 1, on the kinetics of lipase reaction. It is clear that, in that case, consumption of oil speeds up about 8 times as compared to the lipase taken alone, and four times (from 200 to 50 min for 95% volume reduction) as compared to the surfactants taken without the yeast exo-proteins.

Table 1 shows the comparison of the kinetic characteristics of lipase digestion of a 5 µL drop of Prime Burning Peacock Oil obtained by pendant drop method using Kruss tensiometer.

TABLE 1

|  | 1 mg/ml Lipase | 0.75% Example 1 | 0.75% Example 1 And 1 mg/ml Lipase |
|---|---|---|---|
| Initial interfacial tension (IFT, mN/m) | 16.62 | 2.03 | 1.98 |
| Time of 50% Digestion (minutes) | 66 | 605 | 7.9 |
| IFT at 50% Digestion (mN/m) | 10.41 | 1.77 | 1.24 |
| Time of 99% Digestion (minutes) | 418 | 3816 | 50 |
| IFT at 99% Digestion (mN/m) | 4.52 | 1.49 | 0.62 |

Experiment 2

Cellulase activity was determined by measuring glucose formation from cellulotic breakdown of cellulose (11).

Substrate: Watman paper #1

A—Enzyme: TCI Cellulase from *Aspergillus niger*, 5 mg/mL, purified from glucose by ultrafiltration/centrifugation B—SLS: sodium lauryl sulfate, 500 ppm C—Yeast exo-proteins: 500 ppm of yeast exo-protein solution D—Yeast exo-proteins, 500 ppm of yeast exo-protein solution plus 500 ppm of SLS Results Cellulose activity, mg glucose/mg enzyme per hour

| A - Cellulase | Baseline of cellulose activity |
|---|---|
| B - SLS | −40% |
| C - Yeast Exo-proteins | +21% |
| D - Yeast Exo-proteins with SLS | +64% |

SLS alone clearly had an antagonist effect. The yeast exoproteins improved the enzyme activity by 21%. By adding the SLS surfactant, a synergy was observed with the exo-proteins, increasing cellulose activity by 64%.

In one aspect, disclosed herein are compositions comprising an enzyme, and a mix of yeast exo-proteins, where the exo-proteins are derived from the supernatant of a yeast fermentation, and preferably contain stress proteins, and where the stress proteins are produced by exposing live yeast to a stress by the following: thermal, mechanical or combinations thereof, and optionally, the addition of a surfactant.

In some embodiments, in the disclosed compositions the enzyme is an interfacial enzyme, i.e. taken from the following group, or combinations thereof, but not limited to: lipase, cellulose, lignase, polysaccharase and the like, for which the substrate is in the form of water-immiscible material, such as oil, fat, cellulose, lignin, wood chips, etc.

In a further embodiment, the compositions disclosed herein improve the breakdown of cellulosics, starch grains, cell walls, lignin and the like, for ethanol production, paper and pulp processing.

In certain embodiments, the disclosed compositions are used for applications including the following: laundry, spot/stain remover, pre-laundry, dishes, hard surface cleaning, wastewater treatment, cross-flow membranes, soil or water remediation, industrial applications, enhanced oil recovery, textile processing, agricultural chemicals, de-inking of fabrics or paper, softening of cotton, glucose production from cellulosics.

In some embodiments, the surfactant of the present compositions is anionic, nonionic, cationic, zwitterionic or combinations thereof.

The compositions described herein include one or more surfactants at a wide range of concentration levels. Some examples of surfactants that are suitable for use in the detergent compositions described herein include the following:

Anionic: Sodium linear alkylbenzene sulphonate (LABS); sodium lauryl sulphate; sodium lauryl ether sulphates; petroleum sulphonates; linosulphonates; naphthalene sulphonates, branched alkylbenzene sulphonates; linear alkylbenzene sulphonates; alcohol sulphates.

Cationic: Stearalkonium chloride; benzalkonium chloride; quaternary ammonium compounds; amine compounds.

Non-ionic: Dodecyl dimethylamine oxide; coco diethanolamide alcohol ethoxylates; linear primary alcohol polyethoxylate; alkylphenol ethoxylates; alcohol ethoxylates;

EO/PO polyol block polymers; polyethylene glycol esters; fatty acid alkanolamides.

Amphoteric: Cocoamphocarboxyglycinate; cocamidopropylbetaine; betaines; imidazolines.

In addition to those listed above, suitable nonionic surfactants include alkanolamides, amine oxides, block polymers, ethoxylated primary and secondary alcohols, ethoxylated alkylphenols, ethoxylated fatty esters, sorbitan derivatives, glycerol esters, propoxylated and ethoxylated fatty acids, alcohols, and alkyl phenols, alkyl glucoside glycol esters, polymeric polysaccharides, sulfates and sulfonates of ethoxylated alkylphenols, and polymeric surfactants. Suitable anionic surfactants include ethoxylated amines and/or amides, sulfosuccinates and derivatives, sulfates of ethoxylated alcohols, sulfates of alcohols, sulfonates and sulfonic acid derivatives, phosphate esters, and polymeric surfactants. Suitable amphoteric surfactants include betaine derivatives. Suitable cationic surfactants—include amine surfactants. Those skilled in the art will recognize that other and further surfactants are potentially useful in the compositions depending on the particular detergent application.

Preferred anionic surfactants used in some detergent compositions include CalFoam™ ES 603, a sodium alcohol ether sulfate surfactant manufactured by Pilot Chemicals Co., and Steol™ CS 460, a sodium salt of an alkyl ether sulfate manufactured by Stepan Company. Preferred nonionic surfactants include Neodol™ 25-7 or Neodol™ 25-9, which are $C_{12}$-$C_{15}$ linear primary alcohol ethoxylates manufactured by Shell Chemical Co., and Genapol™ 26 L-60, which is a $C_{12}$-$C_{16}$ natural linear alcohol ethoxylated to 60E C cloud point (approx. 7.3 mol), manufactured by Hoechst Celanese Corp.

Several of the known surfactants are non-petroleum based. For example, several surfactants are derived from naturally occurring sources, such as vegetable sources (coconuts, palm, castor beans, etc.). These naturally derived surfactants may offer additional benefits such as biodegradability.

In some embodiments, the yeast fermentation is anaerobic or aerobic fermentation.

In some embodiments, the disclosed compositions are those where the yeast extract is produced by exposing viable yeast to a temperature of between 30° C. to 70° C., preferably between 45° C. to 60° C., for between 2 to 48 hours, preferably between 3 to 5 hours and where the yeast and yeast cell debris are removed after fermentation and stressing processes In some embodiments, the disclosed compositions are those where the yeast is produced by exposing viable yeast to alcohol and temperature elevated to between 30° C. to 70° C., preferably between 45° C. to 60° C., for between 2 and 48 hours, preferably 3 to 5 hours, and where the alcohol is removed after exposure.

In some embodiments, the disclosed compositions further comprise a stabilizer preventing bacterial contamination.

In one embodiment, the composition accelerates the rate of lipase activity in the removal and degradation of oily contamination from a surface or solution.

In a further embodiment, there is an increasing enzymatic hydrolysis of cellulose.

In another embodiment, the enzyme compositions reduce odors.

In another embodiment are methods for improving a cleaning solution with the use of the composition, where the enzyme-extract-surfactant solution can be used in the following applications: laundry, spot remover, pre-laundry, dishes, hard surface cleaning, wastewater treatment, cross-flow membranes, soil or water remediation, industrial applications, enhanced oil recovery, textile processing, agricultural chemicals, flavor industry, cosmetics and perfume applications.

The composition where the enzyme is taken from the following group, or combinations thereof, but not limited to: lipase, cellulase, lignase, polysaccharase and the like, i.e. those enzymes for which the substrate forms a water-immiscible segregated phase.

In a further embodiment, the composition that improves breakdown of cellulosics, starch grains, biological membranes, lignin and the like, for ethanol production, paper and pulp processing.

In some embodiments, the composition further comprises a stabilizer preventing bacterial contamination.

In one embodiment, the composition accelerates the rate of lipase activity in the removal and degradation of oily contamination from a surface or solution.

In a further embodiment, the increased enzyme activity is related to hydrolysis.

References

1. Household & Personal Products Industry—How enzymes can reduce the impact of liquid detergents: one cost-neutral solution is to replace surfactants with a multienzyme solution that improves the environmental impact of a liquid laundry detergent without compromising performance by Anne Merete Nielsen, Teresa J. Neal, Sandra Friis-Jensen, Amulya Malladi (September 2010).
2. Effect of surfactants on cellulose hydrolysis. Steve S. Helle1, Sheldon J. B. Duff1,*, David G. Cooper2, Biotechnology and Bioengineering, 42(5), p. 611-617 (1993). (19 Feb. 2004) © 1993 John Wiley & Sons, Inc. http://onlinelibrary.wiley.com/doi/10.1002/ bit.260420509/abstract
3. Mechanism of surfactant effect in enzymatic hydrolysis of lignocelluloses, T. Eriksson, J. Borjesson, F. Tjerneld, Enzyme and Microbial Technology, 31(3), p. 353-364 (2002). Torny Department of Biochemistry, Lund University, P.O. Box 124, S-221 00 Lund, Sweden. Received 1 Feb. 2002; revised 10 Apr. 2002; Accepted 14 Apr. 2002. Available online 22 May 2002.
4. Hard-Surface Cleaning Using Lipases: Enzyme-Surfactant Interactions and Washing Tests, Encarnación Jurado, et al., J. of Surfactants and Detergents, 10(1), p. 61-70 (2007) . http://lib3.dss.go.th/fulltext/Journal/J.Surfactants %20and %20Detergents/no.1/2007v10n1p61-70.pdf 19 May 2006/ Accepted: 1 Dec. 2006/Published online: 16 Jan. 2007_AOCS 2007.
5. Waterflood improvements by surfactants and water chemistry—Interactions between surfactants and enzymes and possible use for oil recovery, available at www.cipr.uni.no. http://www.cipr.uni.no/ projects.aspx?projecttype=10&project=94.
6. The Colloid Science of Lipids. B. Lindman, B. W. Ninham, Progress in Colloid and Polymer Science, 108, p. 47-57, (1998). 1998, Volume 108/1998, 47-57, DOI: 10.1007/ BFb0117960.
7. Lipase-surfactant interactions P. Skagerlind, et al. Progress in Colloid & Polymer Science, 108, p. 47-57 (1998). http:// www.springerlink.com/content/0273020162t47070/.
8. Regulation of the interfacial activation within the Candida rugosa lipase family. M.A. Permas, et al., J. Phys. Organic Chem., v.22(5), pp. 508-514 (2009).
9. Enhancing effect of Tween-80 on lipase performance in enantioselective hydrolysis of ketoprofen ester. You-Yan Liu, et al., J. Molec. Catalysis B: Enzymatic, v.10(5), pp. 523-529 (2000)
10. Crystallographic Studies on Pancreatic Lipase Activation, Juan A. Hermoso, Departamento de Cristalografía y Biología Estructural, Intituto "Rocasolano"; CSIC, Serrano 119, 28006-Madrid, Spain. http://www.xtal.iqfr.csic.es/ grupo/xjuan/lipasa.html.
11. Pure & Applied Chemistry, Vol. 59, No. 2, pp 257-268, 1987. Measurement of Cellulase Activities, T.K. Ghose, Biochemical Engineering Research Centre, Indian Institute of Technology, New Delhi-110016, India with the following:

References
1. Household & Personal Products Industry - How enzymes can reduce the impact of liquid detergents: one cost-neutral solution is to replace surfactants with a multienzyme solution that improves the environmental impact of a liquid laundry detergent without compromising performance by Anne Merete Nielsen, Teresa J. Neal, Sandra Friis-Jensen, Amulya Malladi (September 2010).
2. Effect of surfactants on cellulose hydrolysis. Steve S. Helle, Sheldon J. B. Duff, David G. Cooper, Biotechnology and Bioengineering, 42(5), p. 611-617 (1993).
3. Mechanism of surfactant effect in enzymatic hydrolysis of lignocelluloses, T. Eriksson, J. Borjesson, F. Tjerneld, Enzyme and Microbial Technology, 31(3), p. 353-364 (2002).
4. Hard-Surface Cleaning Using Lipases: Enzyme-Surfactant Interactions and Washing Tests, Encarnación Jurado, et al., J. of Surfactants and Detergents, 10(1), p. 61-70 (2007).
5. Waterflood improvements by surfactants and water chemistry—Interactions between surfactants and enzymes and possible use for oil recovery. K. Spildo, published at www.cipr.uni.no.
6. The Colloid Science of Lipids, B. Lindman, B. W. Ninham, Progress in Colloid and Polymer Science, 108, p. 47-57, (1998).
7. Lipase-surfactant interactions P. Skagerlind, et al. Progress in Colloid & Polymer Science, 108, p. 47-57 (1998).
8. Regulation of the interfacial activation within the Candida rugosa lipase family. M.A. Permas, et al., J. Phys. Organic Chem., v.22(5), pp. 508-514 (2009)
9. Enhancing effect of Tween-80 on lipase performance in enantioselective hydrolysis of ketoprofen ester. You-Yan Liu, et al., J. Molec. Catalysis B: Enzymatic, v.10(5), pp. 523-529 (2000)
10. Crystallographic Studies on Pancreatic Lipase Activation, Juan A. Hermoso, Departamento de Cristalografía y Biologí, Intituto "Rocasolano"; CSIC, Serrano 119, 28006-Madrid, Spain.
11. Pure & Applied Chemistry, Vol. 59, No. 2, pp 257-268, 1987. Measurement of Cellulase Activities, T.K. Ghose, Biochemical Engineering Research Centre, Indian Institute of Technology, New Delhi-110016, India The following US patents are also referenced:
U.S. Pat. Nos. 5,292,448, 5,447,649, 5,614,484, 5,707,950, 5,776,441, 5,851,973, 5,883,066, 5,935,271, 5,955,416, 5,967,157, 6,017,866, 6,066,611, 6,071,356, 6,133,227, 6,140,295, 6,322,595, 6,436,696, 6,465,410, 6,468,955, 6,624,132, 6,858,212, 6,881,712, 7,156,514, 7,297,224, 7,374,921, 7,419,809, 7,569,528, 7,604,967, 7,709,436, 7,741,093, 7,790,666, 7,902,138, 8,110,389, 20020032142, 20090217463, 20100162491, 20110237486.

What is claimed is:
1. A composition comprising:
  i. non-enzymatic exo-proteins derived from a yeast fermentation process,
  ii. a surfactant selected from the consisting of an anionic, nonionic, cationic, zwitterionic surfactant or combinations thereof, and
  iii. an enzyme component comprising lipase; and
  wherein the composition forms a water-immiscible segregated phase and the rate of enzyme activity on the surface or in the solution is compared to a rate of enzyme activity in the absence of the non-enzymatic exo-proteins and the surfactant.
2. The composition of claim 1, wherein the yeast is *Saccharomyces cerevisiae*.
3. The composition of claim 1, wherein the fermentation process is aerobic.
4. The composition of claim 1, wherein the fermenting yeast is subject to a stress condition.
5. The composition of claim 4, wherein the stress is a nonlethal heat shock.
6. The composition of claim 1, wherein the enzyme further comprises cellulase, lignase, polysaccharase or combinations thereof.
7. The composition of claim 1, further comprising that the yeast exo-proteins are provided from an extract that is produced by exposing viable fermenting yeast to a temperature of between 30° C. to 70° C., for between 2 to 48 hours, and where the yeast and yeast cell debris are removed after fermentation and stressing processes.

8. The composition of claim 1, wherein the yeast exo-proteins are provided from an extract that is produced by exposing viable yeast to alcohol and temperature elevated to between 30° C. to 70° C., for between 2 and 48 hours, and where the alcohol is removed after exposure.

9. The composition of claim 1, further comprising a stabilizer preventing bacterial contamination.

10. A method of accelerating the rate of lipase activity on a surface or in a solution, comprising:
   a) contacting the surface or the solution with a composition comprising,
      i. non-enzymatic exo-proteins derived from a yeast fermentation process,
      ii. a surfactant selected from the consisting of an anionic, nonionic, cationic, zwitterionic surfactant or combinations thereof, and
      iii. an enzyme component comprising lipase; and
   wherein the composition forms a water-immiscible segregated phase and the rate of enzyme activity on the surface or in the solution is compared to a rate of enzyme activity in the absence of the non-enzymatic exo-proteins and the surfactant.

11. The method of claim 10, wherein the lipase activity rate is accelerated in an application selected from: laundry, spot/stain remover, pre- laundry, dishes, hard surface cleaning, wastewater treatment, cross-flow membranes, soil or water remediation, industrial applications, enhanced oil recovery, textile processing, agricultural chemicals, deinking of fabrics or paper, softening of cotton, glucose production from cellulosics.

12. The method of claim 10, wherein the acceleration of the rate of enzyme lipase activity reduce odors.

13. A method of increasing catalytic activity of an interfacial hydrolytic enzyme, oxidizing enzyme or a combination thereof with substrates forming a water-immiscible segregated phase, the method comprising:
   a) contacting the interfacial hydrolytic enzyme, oxidizing enzyme or the combination with a composition comprising:
      i. non-enzymatic exo-proteins derived from a yeast fermentation process,
      ii. a surfactant selected from the consisting of an anionic, nonionic, cationic, zwitterionic surfactant or combinations thereof, and
      iii. an enzyme component comprising lipase; and
   wherein the rate of enzyme activity of the interfacial hydrolytic enzyme, oxidizing enzyme or the combination is compared to a rate of enzyme activity in the absence of the non enzymatic exo-proteins and the surfactant.

14. The method of claim 10, wherein the yeast is *Saccharomyces cerevisiae*.

15. The method of claim 10, wherein the fermenting yeast is subject to a stress condition comprising a non-lethal heat shock.

16. The method of claim 10, wherein the enzyme further comprises cellulase, lignase, polysaccharase or combinations thereof.

17. The method of claim 10, further comprising that the yeast exo-proteins are provided from an extract that is produced by exposing viable fermenting yeast to a temperature of between 30 ° C. to 70 ° C., for between 2 to 48 hours, and where the yeast and yeast cell debris are removed after fermentation and stressing processes.

18. The method of claim 17, wherein the temperature is between 45° C. to 60° C., for between 3 to 5 hours, and where the yeast and yeast cell debris are removed after fermentation and stressing processes.

19. The composition of claim 7, wherein the temperature is between 45° C. to 60° C., for between 3 to 5 hours, and where the yeast and yeast cell debris are removed after fermentation and stressing processes.

* * * * *